United States Patent [19]

Brunelle

[11] Patent Number: 5,081,298
[45] Date of Patent: Jan. 14, 1992

[54] BIS(PENTAALKYLGUANIDINIUM) ALKANE SALTS AS PHASE TRANSFER CATALYSTS

[75] Inventor: Daniel J. Brunelle, Scotia, N.Y.

[73] Assignee: General Electric Company, Schenectady, N.Y.

[21] Appl. No.: 626,147

[22] Filed: Dec. 12, 1990

[51] Int. Cl.$^5$ .................................... C07C 279/04
[52] U.S. Cl. .................................... 564/236; 502/167
[58] Field of Search ........................ 564/236; 502/167

[56] References Cited

U.S. PATENT DOCUMENTS

| | | | |
|---|---|---|---|
| 2,219,350 | 10/1940 | Walden | 564/236 |
| 4,339,459 | 7/1982 | Diery et al. | 564/236 |
| 4,567,174 | 1/1986 | Edwards et al. | 564/236 |
| 4,806,286 | 2/1989 | Senet et al. | 502/167 |

FOREIGN PATENT DOCUMENTS

| | | | |
|---|---|---|---|
| 2595959 | 9/1987 | France | 502/167 |
| 0017918 | 2/1981 | Japan | 502/162 |

Primary Examiner—Glennon H. Hollrah
Assistant Examiner—Susan P. Treanor
Attorney, Agent, or Firm—William H. Pittman; James C. Davis, Jr.

[57] ABSTRACT

α,ω-Bis(pentaalkylguanidinium) alkane salts such as 1,6-bis (penta-n-butylguanidinium) hexane dibromide are prepared by the reaction of a tetraalkyl urea with phosgene or phosphorus oxychloride, or by the reaction of a tetraalkyl thiourea with an N-N-diaalkylcarbamoyl halide, to yield a chloroformamideinium salt, followed by reaction of said salt with a monoalkylamine and reaction of the resulting pentaalkylguanidinium salt with an alkylene dihalide. Said salts are useful as phase transfer catalysts.

9 Claims, No Drawings

BIS(PENTAALKYLGUANIDINIUM) ALKANE SALTS AS PHASE TRANSFER CATALYSTS

This invention relates to novel α, ω-bis(pentaalkylguanidinium)alkane salts and their use as phase transfer catalysts in the preparation of organic compounds by the reaction of polar with non-polar compounds.

Various methods are known for conducting reactions between highly polar reagents, such as alkali metal salts of hydroxyaromatic compounds or thio analogs thereof, and substantially non-polar reagents such as activated halo- or nitro-substituted aromatic compounds. Typical nucleophilic aromatic substitution reactions of this type result in replacement of the halo or nitro group with an aryloxy or arylthio group.

Such nucleophilic aromatic substitution reactions are particularly useful commercially for the preparation of aromatic ether bisimides such as those of 2,2-bis[4-(dicarboxyphenoxy)phenyl]propane bisimides and 4,4'-bis(dicarboxyphenoxy)biphenyl bisimides. These bisimides may be prepared by the reaction of salts of bisphenol A and of 4,4'-biphenol with N-alkylnitro- or N-alkylhalophthalimides. They may be converted to dianhydrides, which in turn undergo reaction with diamines to produce polyetherimides. Certain bisimides also react directly with diamines to produce polyetherimides, as disclosed, for example, in U.S. Pat. No. 4,578,470. The analogous monoimides are similarly useful as endcapping or chain-stopping agents for polyimides.

In most cases, it was formerly necessary to conduct reactions of this type (including nucleophilic displacement reactions) in polar aprotic solvents, since the alkali metal salts are typically insoluble in non-polar solvents. Commercial preparation of aromatic ethers was therefore inhibited by various disadvantages of polar aprotic solvents, including high cost, difficulty of recycling and toxicity.

More recently, it has been possible to conduct the reaction in non-polar solvents with the employment of a phase transfer catalyst, facilitating incorporation of the salt of the hydroxyaromatic compound in the organic phase. Many types of phase transfer catalysts are known, including quaternary ammonium and phosphonium salts as disclosed in U.S. Pat. No. 4,273,712. More specifically, there have been used various bis-quaternary ammonium or phosphonium salts as disclosed in U.S. Pat. No. 4,554,357, and aminopyridinium salts as disclosed in U.S. Pat. Nos. 4,460,778, 4,513,141 and 4,681,949.

Despite the improvements afforded by the use of phase transfer catalysts as described in the above-identified patents, several problems remain. In the first place, the reaction is often quite slow when those catalysts are employed. In the second place, yields are often very low, particularly when halophthalimides are employed. In the third place, decomposition of the phase transfer catalyst usually occurs during the reaction, necessitating frequent replacement thereof and resulting in the formation of by-products which cause discoloration of the product and may lead to undesirable side reactions.

The low yields encountered with the use of halophthalimides are illustrated by the reaction of 4-chloro-N-methylphthalimide with bisphenol A disodium salt in the presence of 1,6-bis(tri-n-butylammonium)hexane dibromide, which yields 2,2-bis[4-(3,4-dicarboxyphenoxy)phenyl]propane bis-N-methylimide in only 5% yield after 2-¾ hours. By contrast, the yield is greater than 95% after 30 minutes using the 4-nitro compound.

Catalyst decomposition is particularly noticeable in the preparation of 4,4'-bis(dicarboxyphenoxy)biphenyl bisimides by the reaction of nitrophthalimides with 4,4'-biphenol salts, using a bis(trialkylammonium)alkane dihalide as catalyst. When the reaction is conducted in refluxing toluene as solvent, high yields are obtained. However, in xylene (which has a higher boiling point) the yield is much lower if the catalyst is exposed to reflux temperatures prior to initiation of the reaction, in the course of drying the nitrophthalimide. Yields increase somewhat if the catalyst is not introduced until after drying, but are still lower than desired.

In copending application Ser. No. 07/626,150, filed Dec. 12, 1990, now abandoned, there is disclosed and claimed a process in which various hexaalkylguanidinium and α, ω-bis(pentaalkylguanidinium)alkane salts are employed as phase transfer catalysts in reactions between polar and non-polar compounds. The use of these salts frequently increases the reaction rate and yield substantially as compared with the use of previously known phase transfer catalysts in comparable amounts. In addition, said guanidinium salts have a high degree of thermal stability and thus do not undergo substantial decomposition during the displacement reaction. This means less color formation in the product and the potential for recycling of catalyst, decreasing the cost of the process.

Accordingly, the present invention includes α, ω-bis(pentaalkylguanidinium)alkane salts having the formula

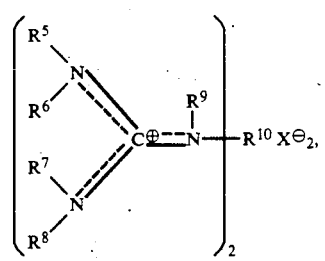

wherein each of $R^5$, $R^6$, $R^7$, $R^8$ and $R^9$ is a primary alkyl radical, $R^{10}$ is a bis(primary alylene) radical and X is an anion. For the sake of brevity, said salts are hereinafter sometimes designated "guanidinium salt".

The alkyl radicals suitable as $R^{5-9}$ in formula I are primary alkyl radicals, generally containing about 1–12 and preferably about 2–6 carbon atoms. $R^{10}$ is usually a $C_{2-12}$ and preferably a $C_{4-8}$ alkylene radical in which the terminal carbons are primary; most preferably, it is straight chain alkylene.

The X value may be any anion and is preferably an anion of a strong acid; examples are chloride, bromide and methanesulfonate. Chloride and bromide ions are usually preferred.

As indicated by the dotted bonds in formula I, each positive charge in the guanidinium salt is delocalized over one carbon and three nitrogen atoms. This is believed to contribute to the salt's stability under the conditions encountered when said salts are used as phase transfer catalysts, including relatively high temperatures. As a result, decomposition of the guanidinium salts of this invention does not occur or occurs only to a very minor extent. The results include suppression of by-product formation and potential for continued use via recycle.

The guanidinium salts of this invention may be prepared by (1) the reaction of a tetraalkylurea with phosgene or phosphorus oxychloride, or by the reaction of a tetraalkylthiourea with an N,N-dialkylcarbamoyl halide, to yield a chloroformamidinium salt, frequently referred to as a "Vilsmeier salt", followed by (2) reaction of said salt with a monoalkylamine and (3) reaction of the resulting pentaalkylguanidinium salt with an alkylene dihalide The reaction conditions are similar to those disclosed in Kantlehner et al., *Liebigs Ann. Chem.*, 1084, 108–126, and Pruszynski, *Can. J. Chem.*, 65, 626–629 (1987), which are incorporated by reference herein.

More specifically, reaction (1) may be conducted at a temperature in the range of about 50°–100° C., employing a molar ratio of phosphorus oxychloride to tetraalkylurea of about 1.0–1.1:1. Reaction (2) proceeds advantageously at temperatures in the range of about 0°–75° C., with a molar ratio of amine to Vilsmeier salt in the range of about 2.25–2.5:1; and reaction (3) at temperatures in the range of about 70°–100° C., with molar ratios of pentaalkylguanidine to alkylene dihalide at or near 2:1. In all three reactions, a polar organic solvent such as acetonitrile is often preferably employed The preparation of the guanidinium salts of this invention is illustrated by the following examples.

EXAMPLE 1

A mixture of 56.9 grams (200 mmol.) of tetra-n-butylurea, 32.2 grams (210 mmol.) of phosphorus oxychloride and 75 ml. of acetonitrile was heated at 75° C. in a nitrogen atmosphere for one hour. The mixture was then cooled to 0° C. and 33.6 grams (460 mmol.) of n-butylamine was added over 15 minutes with stirring, whereupon a soft, fluffy precipitate formed. The mixture was warmed to 60° C. for one hour and again cooled to 0° C., quenched with 50 ml. of 25% (by weight) aqueous sodium hydroxide solution and extracted with ether. The ether extracts were dried over magnesium sulfate, filtered and stripped to give a pale yellow oil which, upon distillation, yielded 56.32 grams (83% of theoretical) of penta-n-butylguanidine.

A mixture of 16.98 grams (50 mmol) of penta-n-butylguanidine, 6.0995 grams (25 mmol.) of 1,6-dibromohexane and 50 ml. of acetonitrile was heated under reflux in a nitrogen atmosphere for 16 hours, after which proton nuclear magnetic spectroscopy showed the absence of carbon-bromine absorption. Upon vacuum stripping, a pale yellow oil was obtained which crystallized to a white solid upon standing. Upon recrystallization from a mixture of hexane and ethyl acetate, the desired 1,6-bis(N,N',N',N'',N''-penta-n-butylguanidinium)hexane dibromide, which melted at 100°–102° C.; its structure was confirmed by proton and carbon-13 nuclear magnetic resonance and Fourier transform infrared spectroscopy.

EXAMPLE 2

The procedure of Example 1 was repeated, substituting tetraethylurea on an equimolar basis for the tetra-n-butylurea and employing a mixture of 25 mmol. each of n-butylamine and triethylamine, the latter serving as a hydrogen chloride acceptor. The product was the desired 1,6-bis(N-n-butyl-N',N',N'',N''-tetraethylguanidinium)hexane dibromide.

The guanidinium salts of this invention are capable of use as phase transfer catalysts in an extremely broad spectrum of reactions between organic chemicals. In general, they may advantageously be employed in any situation where reaction is to be effected between one reagent which is highly polar and insoluble in the non-polar liquid to be used as solvent, and another which is substantially non-polar and is soluble therein. More particularly, they are employable in nucleophilic aromatic substitution reactions, and still more particularly in reactions between at least one alkali metal salt of a hydroxyaromatic compound or thio analog thereof and at least one activated halo- or nitro-substituted aromatic compound. For the sake of convenience, these reagents will be the principal ones hereinafter and they will be specifically identified as "phenol salt" and "activated aromatic compound", respectively.

The phenol salts are generally compounds of the formula

wherein $R^1$ is an aromatic radical containing about 6–30 carbon atoms, M is an alkali metal, Z is oxygen or sulfur and a is 1 or 2. The $R^1$ radical may be a hydrocarbon radical or may contain other atoms such as oxygen or sulfur. Illustrative monovalent radicals (i.e., those derived from compounds in which a is 1) include phenyl, m-tolyl, p-tolyl, 1-naphthyl, 2-naphthyl, p-chlorophenyl and 4-bromo-1-naphthyl.

Most often, $R^1$ is a divalent aromatic radical; i.e., a is 2. Illustrative dihydroxyaromatic compounds are resorcinol, hydroquinone, 4,4'-dihydroxybiphenyl, 4,4'-dihydroxy-3,3',5,5'-tetramethylbisphenyl, bis(4-hydroxyphenyl)methane, 3-hydroxyphenyl-4-hydroxyphenylmethane, 2,2-bis(2-hydroxyphenyl)propane, 2,2-bis(4-hydroxyphenyl)propane (hereinafter "bisphenol A"), 2-(3-hydroxyphenyl)-2-(4-hydroxyphenyl)propane, 1,1-bis(4-hydroxyphenyl)ethane, 2,2-bis(4-hydroxyphenyl)pentane, 1,1-bis(4-hydroxyphenyl)ethylene, 4,4'-dihydroxybnnzophenone, bis(4-hydroxyphenyl)ether, bis(4-hydroxyphenyl) sulfide, bis(4-hydroxyphenyl) sulfoxide, bis(4-hydroxyphenyl) sulfone and 3-hydroxyphenyl-4-hydroxyphenyl sulfone.

The preferred $R^1$ radicals are usually

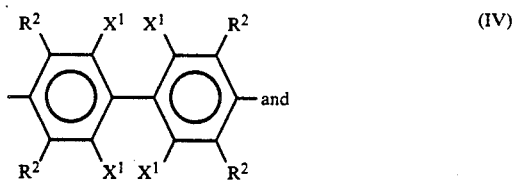

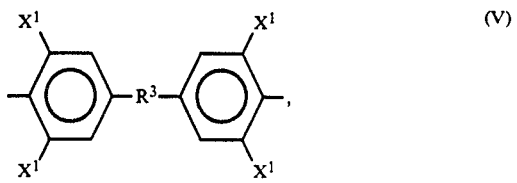

wherein each $R^2$ is independently hydrogen or methyl, $R^3$ is a straight-chain or branched alkylene radical containing 1-5 carbon atoms and each $X^1$ is independently hydrogen or halogen (usually chlorine or bromine). Mixtures of the foregoing formulas are also contemplated. Especially desirable are the bisphenol A salts, having formula V in which $R^3$ is isopropylidene and each $X^1$ is hydrogen.

The alkali metal in the phenol salt may be any of the known alkali metals. Sodium and potassium are usually preferred by reason of availability and low cost, with sodium being especially preferred. The Z value may be oxygen or sulfur and is usually oxygen.

By "activated aromatic compound" is meant a compound having an electron-deficient aromatic ring, generally achieved by the presence of one or more electron-withdrawing substituents. Illustrative substituents of this type are halo, nitro, acyl, cyano, carboxy, carbalkoxy, aldehydo, sulfone and perfluoroalkyl, as well as heterocyclic aromatic substituents such as pyridyl.

Most often, the activated aromatic compound is a substituted imide having the formula

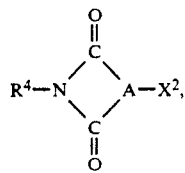

(VI)

wherein A is an aromatic radical, $R^4$ is hydrogen or an unsubstituted or substituted hydrocarbon radical containing about 1-13 carbon atoms and $X^2$ is halo or nitro. The A radical generally contains about 6-30 carbon atoms. The imide is generally derived from an o-dicarboxylic acid such as phthalic acid or 2,3-naphthalenedicarboxylic acid; however, derivatives of acids such as 1,8-naphthalenedicarboxylic acid are also suitable. Most preferably, the imide is a phthalimide.

The $R^4$ value is preferably an alkyl and especially a lower alkyl radical (i.e., one containing up to 7 carbon atoms). Most preferably, $R^4$ is methyl or n-butyl.

The reaction between the phenol salt and the substituted aromatic compound is conducted in a non-polar organic solvent. Suitable solvents include benzene, toluene, xylene, chlorobenzene, o-dichlorobenzene, chlorotoluene, dichlorotoluene and octane. Aromatic solvents are preferred, with aromatic hydrocarbon solvents and especially toluene being particularly preferred.

The reaction mixture containing the phenol salt, activated aromatic compound, guanidinium salt and solvent is normally heated at a temperature in the range of about 100°-200° C., preferably about 125°-175° C. It is preferred to use stoichiometric amounts of the phenol salt and activated aromatic compound, but under appropriate conditions an excess of one reagent or the other (especially the phenol salt), generally not more than about 25%, may be employed. An internal standard may be incorporated in the reaction mixture for analytical purposes. The proportion of guanidinium salt is a catalytically effective proportion, most often about 0.25-2.5 mole percent based on activated aromatic compound. In the case of a compound containing both halo and nitro substituents, the halo substituent is normally displaced.

When isolation of the product is required, it may be achieved by conventional methods. These typically involve washing with an aqueous alkaline solution followed by drying of the organic phase and solvent stripping.

The employment of the guanidinium salts of this invention as phase transfer catalysts is illustrated by the following examples All percentages are by weight. "Chromatographic yield" is yield as determined by high pressure liquid chromatography.

EXAMPLE 3

Sodium p-cresoxide was prepared by the reaction of p-cresol with sodium hydroxide in aqueous solution, followed by addition of toluene and removal of water by azeotropic distillation. A mixture of 780 mg. (6 mmol.) of sodium p-cresoxide and 800 mg. (5 mmol.) of p-chloronitrobenzene was prepared in an anhydrous nitrogen atmosphere, and there were added 20 ml. of chlorobenzene, 2 ml. of toluene and a small amount of tetracosane as an internal standard. The toluene was removed by distillation in a nitrogen atmosphere, with stirring, to effect azeotropic drying of the reactants. 1,6-Bis(penta-n-butylguanidinium)hexane dibromide was then added as a stock solution in o-dichlorobenzene, in the amount of 0.25 mole percent based on p-chloronitrobenzene, and heating at 140° C. and stirring were continued for 30 minutes. At the end of this time, the yield of p-nitrophenyl cresyl ether was 93% as determined by vapor phase chromatography.

EXAMPLE 4

A 50-ml. round-bottomed flask fitted with a magnetic stir bar, condenser and nitrogen inlet was charged with 1.458 grams (5.35 mmol.) of bisphenol A disodium salt, 3.021 grams (10.7 mmol.) of 4-bromo-N-n-butylphthalimide, 0.27 mmol. of 1,6-bis(penta-n-butylguanidinium)-hexane dibromide, 206.3 mg. of 1,3,5-triphenylbenzene as an internal standard and 3.2 ml. of o-dichlorobenzene. The mixture was heated at 170° C., with stirring, and periodically sampled. After 30 minutes, analysis of a sample by high pressure liquid chromatography showed the formation of 2,2-[4-(3,4-dicarboxyphenoxy)phenyl]propane bis-N-n-butylimide in 93% yield. A control run under similar conditions but using twice the molar amount of 1,6-bis(tri-n-butylammonium)hexane dibromide gave a yield of only 20% after 3 hours.

What is claimed is:

1. An α, ω-bis(pentaalkylguanidinium)alkane salt having the formula

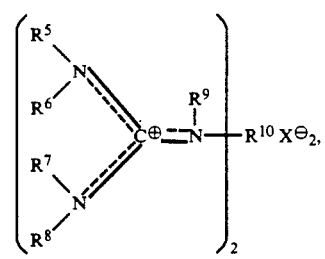

(I)

wherein each of $R^5$, $R^6$, $R^7$, $R^8$ and $R^9$ is a primary alkyl radical, $R^{10}$ is a bis(primary alkylene) radical and X is an anion.

2. A salt according to claim 1 wherein each of $R^{5-9}$ contains about 2-6 carbon atoms.

3. A salt according to claim 2 wherein $R^{10}$ is a $C_{2-12}$ straight chain alkylene radical.

4. A salt according to claim 3 wherein X is chloride or bromide.

5. A salt according to claim 4 wherein $R^{10}$ is 1,6-hexylene.

6. A salt according to claim 5 wherein each of $R^{5-9}$ is n-butyl.

7. A salt according to claim 6 wherein X is bromide.

8. A salt according to claim 5 wherein each of $R^{5-8}$ is ethyl and $R^9$ is n-butyl.

9. A salt according to claim 8 wherein X is bromide.

* * * * *